United States Patent [19]
Michaelis

[11] Patent Number: 5,979,244
[45] Date of Patent: Nov. 9, 1999

[54] METHOD AND APPARATUS FOR EVALUATING INTERNAL FILM STRESS AT HIGH LATERAL RESOLUTION

[75] Inventor: Alexander Michaelis, Wappingers Falls, N.Y.

[73] Assignee: Siemens Aktiengesellschaft, Munich, Germany

[21] Appl. No.: 09/034,517

[22] Filed: Mar. 4, 1998

[51] Int. Cl.$^6$ .............................. G01L 1/24; G01M 9/00
[52] U.S. Cl. ................................ 73/800; 73/849
[58] Field of Search .......................... 73/800, 818, 826, 73/812, 849

[56] References Cited

U.S. PATENT DOCUMENTS

| | | | |
|---|---|---|---|
| 4,841,778 | 6/1989 | Butler et al. ........................ | 73/800 |
| 5,232,547 | 8/1993 | Drowley et al. ..................... | 117/55 |
| 5,546,811 | 8/1996 | Rogers et al. ...................... | 73/800 |
| 5,864,393 | 1/1999 | Maris ................................. | 356/28 |

*Primary Examiner*—Max Noori
*Attorney, Agent, or Firm*—Stanton C. Braden

[57] ABSTRACT

Methods and apparatus for evaluating internal film stress on a sample at high lateral resolutions are provided. The sample comprises at least one material and has a planar or smooth surface. To determine internal stress, a calibration curve correlating a set of first ellipsometric parameter amplitudes to a set of first stress values is generated. One first stress value is correlated to one first ellipsometric amplitude. Then, the sample for which stress is to be determined is rotated as a function of sample rotation angle a and is measured for a set of second ellipsometric parameter at a selected area of the sample to determine a second ellipsometric amplitude. The internal stress at the selected area of the sample is then determined from the calibration curve by using the second ellipsometric amplitude as an index to determine a corresponding stress value from the calibration curve.

55 Claims, 8 Drawing Sheets

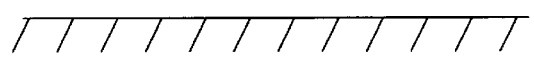
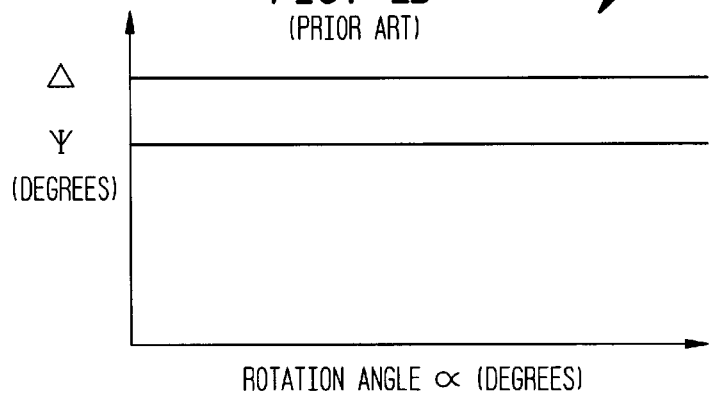
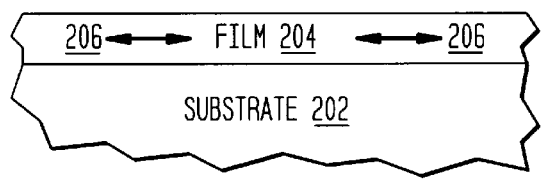
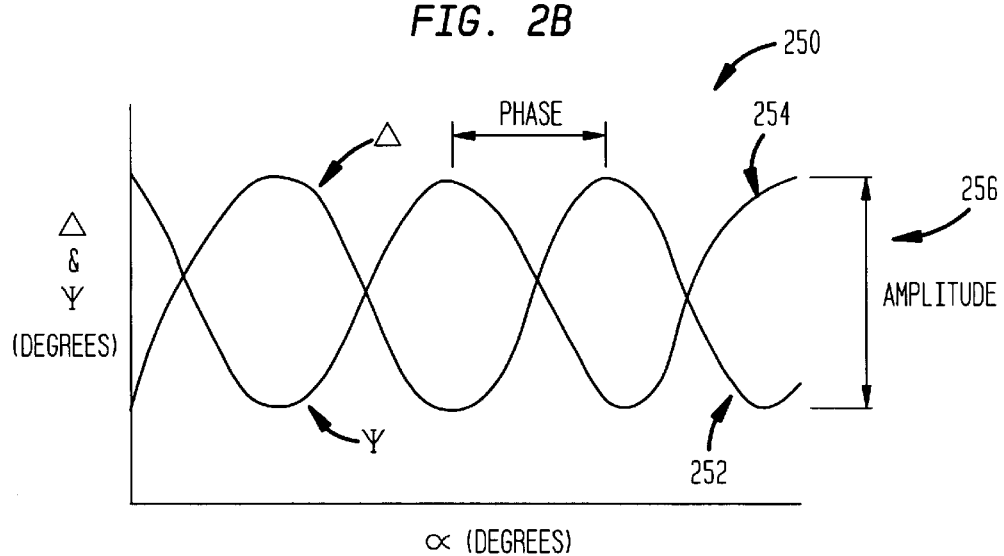

METHOD AND APPARATUS FOR EVALUATING INTERNAL FILM STRESS AT HIGH LATERAL RESOLUTION

BACKGROUND OF THE INVENTION

The present invention relates to internal film stress evaluation. More particularly, the present invention relates to internal film stress evaluation using revolving ellipsometry at high lateral resolution.

Today's semiconductor fabrication technology typically employs more than one layer of film (e.g., multi-layer systems) to put more features into integrated circuit (IC) chips. In general, films in these multi-layer systems induce internal film stress due to lattice mismatch at the interfaces of such layers. In addition, different mechanical material properties such as elasticity, thermal expansion and the like also contribute to the internal film stress. It should be appreciated that the term "film" as used herein refers to a material having a smooth or planar surface. The film may be comprised of a uniform material or mixed materials in the shape of, for example, a substrate, a membrane, a layer, a stratum, a sheet, or any form that includes a smooth or planar surface. A sample or system may be comprised of one or more films and are used interchangeably herein.

Stress in a film is undesirable because the stress often leads to serious degradation of the material properties of the film. For example, a stressed multi-layer system may lose its intended electrical characteristics. Further, stress may induce dislocations at the top of deep trenches. In a memory chip such as dynamic random-access-memory (DRAM), for instance, the dislocations can cause variable retention time of electrical signals. Accordingly, accurate evaluation of stress is crucial in order to minimize and understand the effect of internal stress.

In the past, conventional techniques typically determined internal film stress only on bendable materials. In particular, the conventional techniques measured the bending or curvature of a macroscopic uniform sample (e.g., a wafer, a substrate, etc.) using optical (e.g., beam deflection) or electrical (e.g., capacity) techniques. For example, a beam of light is directed on the bendable sample and a curvature radius between the angles of incidence and reflection on the sample is measured. Then, a film is deposited on the bendable sample. The deposited film induces the sample to bend. A beam of light is then directed on the bent sample and a curvature radius between the angles of incidence and reflection on the bent sample is measured. The difference between the radius obtained before the layer deposition and the radius after the deposition is then computed to obtain a difference term. The stress is then determined by correlating the difference term using the well known Stoney's formula by applying known elastic constants of the sample material.

Unfortunately, these conventional techniques have several drawbacks that limit their application. For example, the conventional approaches cannot be used on unbendable samples or solid samples that are too massive to show any bending. Further, these techniques require macroscopic uniform samples. In addition, since these techniques are designed for macroscopic uniform samples, they cannot be applied at high lateral resolutions necessary for analyzing microscopic features. For example, patterned materials typically exhibit a sensitive and microscopic geometry. In a patterned material, stress gradients occur at internal edges and vertical sidewalls of trench structures. Stress peaks typically occur at an edge of a trench and may cause a dislocation.

In view of the foregoing, what is desired is a method and apparatus for evaluating internal film stress on any samples including unbendable or solid samples at high lateral resolution.

SUMMARY OF THE INVENTION

The present invention provides methods and apparatus for evaluating internal film stress on a sample at high lateral resolution. The sample comprises at least one material and has a planar or smooth surface.

In one aspect of the present invention, a calibration curve correlating a set of first ellipsometric parameter amplitudes to a set of first stress values is generated. One first stress value is correlated to one first ellipsometric amplitude. Then, the sample for which stress is to be determined is rotated as a function of sample rotation angle $\alpha$ and is measured for a set of second ellipsometric parameter at a selected area of the sample to determine a second ellipsometric amplitude. The internal stress at the selected area of the sample is then determined from the calibration curve by using the second ellipsometric amplitude as an index to determine a corresponding stress value from the calibration curve.

In another embodiment of the present invention, ellipsometric parameters $\Delta$ and $\psi$ are measured at a selected area of the sample as a function of sample rotation angle $\alpha$ by rotating the sample to generate ellipsometric parameter curves $\Delta(\alpha)$ and $\psi(\alpha)$. The sample is characterized by a stress optical coefficient tensor c. The thickness d of the sample at the selected area of the sample is also determined. The ellipsometric parameter curves $\Delta(\alpha)$ and $\psi(\alpha)$ are used to determine a dielectric tensor $\bar{n}$. From these values, namely, $\bar{n}$, c, and d, the present embodiment determines internal stress, s, in accordance with equation, $\bar{n} = c\, s\, d$, where $\bar{n}$ is the dielectric tensor, c is the stress optical coefficient tensor, s is the desired stress, and d is the thickness of the sample at the selected area of the sample.

In yet another embodiment of the present invention, an apparatus for measuring internal film stress on an anisotropic sample at high lateral resolutions is provided. The apparatus comprises an ellipsometer and a rotating stage rotatably disposed below the ellipsometer for rotating the sample so as to vary an angle of rotation a about a center of rotation axis. The ellipsometer measures ellipsometric parameters $\Delta$ and $\psi$ by directing a linearly polarized incident light onto a selected area of the sample to generate an elliptically polarized reflected light. The ellipsometer then compares the linearly polarized incident light and the elliptically polarized reflected light to measure the ellipsometric parameters $\Delta$ and $\psi$. In this configuration, the center of rotation axis is aligned with the ellipsometer so that the ellipsometer correlates the ellipsometric $\Delta$ and $\psi$ angles to the angle of rotation $\alpha$. The resulting ellipsometric parameter curves $\Delta(\alpha)$ and $\psi(\alpha)$ are used to determine the stress at the selected area of the sample at high lateral resolution.

These and other advantages of the present invention will become apparent upon reading the following detailed descriptions and studying the various figures of the drawings.

BRIEF DESCRIPTION OF THE DRAWINGS

The features of the present invention may best be understood by reference to the following description of the presently preferred embodiments together with the accompanying drawings:

FIG. 1A illustrates an isotropic substrate comprising a single layer of uniform material.

FIG. 1B illustrates a graph depicting the relationship of ellipsometric angles Δ and ψ as a function of the angle of rotation of an isotropic substrate around its surface normal.

FIG. 2A illustrates an exemplary sample under stress comprised of a film layer disposed over a substrate with resulting internal film stress.

FIG. 2B illustrates a graph of ellipsometric parameter Δ and ψ as a function of the angle of rotation a of a sample under stress in accordance with the present invention.

DETAILED DESCRIPTION OF THE PREFERRED EMBODIMENTS

Figure 3A:
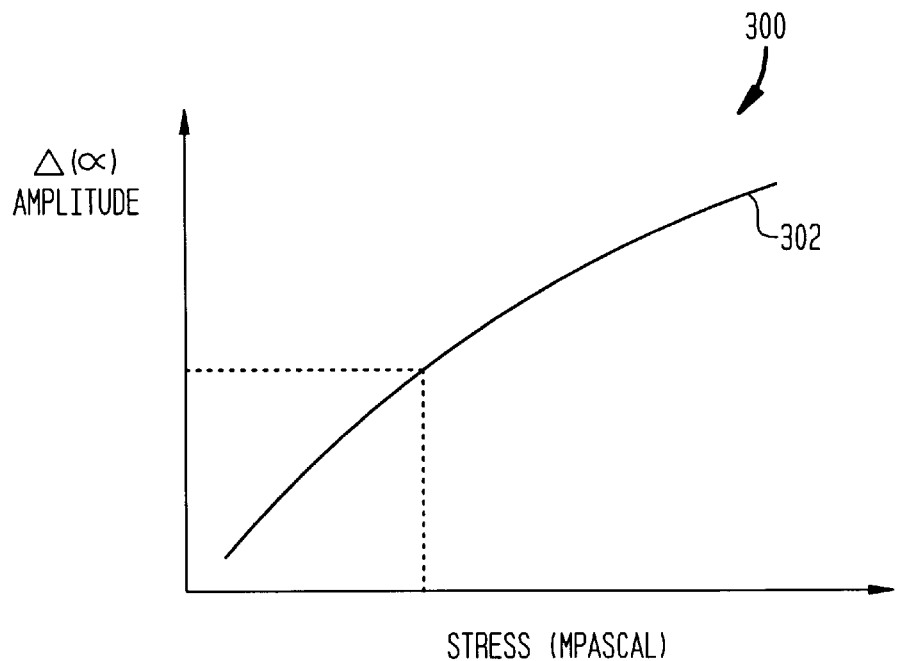
FIG. 3A illustrates, in accordance with the present invention, an exemplary calibration curve correlating a plurality of amplitudes between maximum and minimum ellipsometric parameter Δ to a plurality of stress values.

An invention is described for providing methods and apparatus for evaluating internal film stress on a sample at high lateral resolution. In the following description, numerous specific details are set forth in order to provide a thorough understanding of the present invention. It will be obvious, however, to one skilled in the art, that the present invention may be practiced without some or all of these specific details. In other instances, well known process steps have not been described in detail in order not to unnecessarily obscure the present invention.

The present invention determines internal film stress on a sample including an unbendable sample, a bendable sample, a solid sample, or a sample for which high lateral resolution stress measurement is needed. Some exemplary samples include dynamic random-access-memory (DRAM) chips, semiconductor wafer stacks comprising a plurality of layers, integrated circuit chips, etc. A sample or system, may be comprised of one or more films. Within the sample or system context, a film is any material, preferably solid, having a smooth or planar surface and may be comprised of a uniform material or mixed materials in the shape of, for example, a substrate, a membrane, a layer, a stratum, a sheet, or any form that includes a smooth or planar surface.

In the present invention, internal film stress on a sample at high lateral resolution is determined based on revolving ellipsometry by measuring and correlating the optical properties as the sample is rotated. In particular, the present invention rotates the sample over a rotation angle α and measures a set of ellipsometric parameters Δ and ψ angles as a function of α at a selected area of the sample. The selected area is preferably on the planar or smooth surface of the sample. Analysis of the Δ(α) and ψ(α) curves allows determination of the internal film stress. In this configuration, the present invention focuses a linearly polarized incident light onto the selected area of the sample and measures the ellipsometric parameters Δ and ψ of the corresponding reflected light as a function of α. By utilizing optical methods and apparatus, the lateral resolution is limited only be the refraction of light and the disturbance of the state of polarization, which is about 1 micron.

It should be appreciated that conventional ellipsometry technique has been used mainly to measure the thickness of thin films and other optical parameters such as Δ and ψ angles in a stationary or fixed sample. Conventional ellipsometer is an apparatus that implements the ellipsometry to measure the thickness and other optical parameters in a stationary sample. The non-revolving ellipsometry and ellipsometer are well known in the art and offer the advantage of being non-destructive and non-invasive to a sample.

Unlike conventional ellipsometry, the present invention employs ellipsometry to measure internal film stress. In addition, the present invention modifies the conventional ellipsometry by rotating a sample to determine internal stress in the sample. Using revolving ellipsometry allows evaluation of internal stress on all types of samples including unbendable samples or solid samples at high lateral resolution.

In one aspect of the present invention, internal stress on a sample is evaluated by generating a calibration curve correlating a set of first ellipsometric parameter amplitudes to a set of first stress values. Then, the sample for which stress is to be determined is rotated as a function of sample rotation angle α and is measured for a set of second ellipsometric parameter at a selected area of the sample to determine a second ellipsometric amplitude. The internal stress at the selected area of the sample is then determined from the calibration curve by using the second ellipsometric amplitude as an index to determine a corresponding stress value from the calibration curve.

In another embodiment of the present invention, the internal stress on a sample is determined quantitatively. The current embodiment of the present invention determines the internal stress by rotating the sample and measuring ellipsometric parameters Δ and ψ at a selected area of the sample as a function of sample rotation angle a to generate ellipsometric parameter curves Δ(α) and ψ(α). The dielectric tensor ñ is computed from the ellipsometric parameter curves Δ(α) and ψ(α). The stress optical coefficient is a tensor that may be obtained from a well known table of such values. The thickness of the film layer is also measured.

These values are then used to determine the stress, s, in accordance with equation $\tilde{n}=c\,s\,d$, where $\tilde{n}$ is the dielectric tensor, c is the stress optical coefficient, s is the desired stress, and d is the thickness at the selected area of the sample.

In yet another embodiment, the present invention provides an apparatus for measuring internal film stress on a sample. The apparatus comprises an ellipsometer and a rotating stage. The rotating stage is rotatably disposed below the ellipsometer for rotating the sample to vary the angle of rotation a around a center of rotation axis. The ellipsometer directs a linearly polarized incident light onto a predetermined area of the sample to generate an elliptically polarized reflected light. The ellipsometer then compares the linearly polarized incident light and the elliptically polarized reflected light to measure ellipsometric parameters $\Delta$ and $\psi$. The ellipsometer then correlates the ellipsometric parameters $\Delta$ and $\psi$ to the angle of rotation $\alpha$ to determine the internal stress.

To facilitate discussion, FIG. 1A illustrates a substrate 100 comprising a single layer of uniform material. In this one-layer configuration, substrate 100 is not under any internal film stress associated with another layer and is called an isotropic material due to its uniform optical parameters in all directions. In analytical terms, the optical parameters of isotropic material such as substrate 100 can be described by a complex refraction index, $\tilde{n}$. The complex refraction index, $\tilde{n}$, is defined as the complex unit (n+ik), where n is a refractive index and k is an extinction coefficient. The refractive index, n, describes the phase shift of light penetrating into a material while the extinction coefficient describes the absorption of light into the material or loss of intensity of light penetrating the material. The refractive index n and the extinction coefficient completely describe the optical parameters or behavior of an isotropic material as is well known in the art.

For an optically isotropic substrate, the value of n and k can be determined by measuring two other values: ellipsometric parameters $\Delta$ and $\psi$. The ellipsometric parameters $\Delta$ and $\psi$ have the dimensions of an angle and are typically measured by the well known ellipsometry technique. The ellipsometry measures the elliposometric parameters $\Delta$ and $\psi$ angles by comparing the change in polarization between a linearly polarized incident light and an elliptically polarized reflected light off of an isotropic material. The ellipsometry then coverts these values into the optical parameters n and k using well known formulas as described, for example, in *Ellipsometry and Polarized Light,* R. M. A. Azzam and N. M. Bashava, North Holland Elsevier Science Publishing. Ellipsometers implementing the conventional ellipsometry method are also well known in the art.

FIG. 1B illustrates a graph depicting the relationship of ellipsometric parameters $\Delta$ and $\psi$ angles as a function of the angle of rotation of isotropic substrate 100 around its surface normal. The angle $\alpha$ describes the rotation angle of substrate 100 around the surface normal similar to a CD spinning around its center axis. Since optical parameters for an isotropic material are uniform in all directions, the ellipsometric parameters $\Delta$ and $\psi$ angles remain constant even as substrate 100 is rotated along the surface normal. That is, the rotation of substrate 100 as a function of rotation angle $\alpha$. does not cause variation in ellipsometric parameters $\Delta(\alpha)$ and $\psi(\alpha)$ in an isotropic or unstressed material.

When stress is applied on an isotropic material as by depositing a film on substrate 100, the stress induces the previously isotropic substrate (i.e., sample) to become optically anisotropic. The optical properties of a sample under stress is not uniform in all directions; instead, the optical parameters vary depending on direction. To facilitate discussion, FIG. 2A illustrates an exemplary sample 200 comprised of a film 204 disposed over a substrate 202 with resulting internal film stress 206. It should be appreciated that sample 200 of FIG. 2A shown for illustration purposes only and additional films, which have not been described, may be present above, below, and between the film or substrate shown.

For samples with stress induced anisotropy, the aforementioned isotropic optical parameters are modified. Specifically, the complex refractive index $\tilde{n}$ for anisotropic sample 200 now describes a dielectric tensor as follows:

$$\tilde{n} = \begin{bmatrix} n1+k1 & 0 & 0 \\ 0 & n2+k2 & 0 \\ 0 & 0 & n3+k3 \end{bmatrix}$$

The dielectric tensor n consists of three extinction coefficients k1, k2, and k3 and three refractive indices n1, n2, and n3. Of these, n1 and k1 are often called ordinary refractive index parameters while the n2, k2, n3, and k3 are generally referred to as extra-ordinary refractive index parameters. In another form, the dielectric tensor $\tilde{n}$ is also described by the following permittivity tensor:

$$\varepsilon = \begin{bmatrix} \varepsilon_a & 0 & 0 \\ 0 & \varepsilon_b & 0 \\ 0 & 0 & \varepsilon_c \end{bmatrix}$$

where $\epsilon_{ao}$, $\epsilon_{ao}$, $\epsilon_o$ represent $(n1+k1)^2$, $(n2+k2)^2$, and $(n3+k3)^2$, respectively.

In the present invention, when sample 200 is rotated about its surface normal axis in revolving ellipsometry configuration, the optical parameters of sample 200 change. FIG. 2B illustrates a graph 250 of two curves corresponding to ellipsometric parameters $\Delta$ and $\psi$ as a function of the angle of rotation angle a of sample 200 under stress. As shown in FIG. 2B, the curves of ellipsometric parameters $\Delta$ and $\psi$ vary with the variation in the rotation of sample 200. In particular, the ellipsometric parameters $\Delta$ and $\psi$ angles vary in a sinusoid-like manner. In addition, the ellipsometric parameters $\Delta$ and $\psi$ angles are out of phase from each other.

With reference still to FIG. 2B, each of the curves associated with the ellipsometric parameters $\Delta$ and $\psi$ angles can be characterized by an amplitude between the maximum and minimum values of the respective ellipsometric parameters $\Delta$ and $\psi$. That is, the amplitude for the curve of ellipsometric parameter $\Delta(\alpha)$ angles is the difference between the maximum and minimum $\Delta(\alpha)$ angle values on the curve. Likewise, the amplitude for the curve of ellipsometric parameter $\psi(\alpha)$ angles is the difference between the maximum and minimum $\psi(\alpha)$ angle values on the curve. In the present invention, the ellipsometric parameters $\Delta(\alpha)$ and $\psi(\alpha)$ are measured at high lateral resolutions at a selected area of a sample by focusing a linearly polarized incident light onto the selected area and then measuring the ellipsometric angles $\Delta$ and $\psi$ of corresponding reflected light as a function of rotating angle $\alpha$.

Figure 3B:
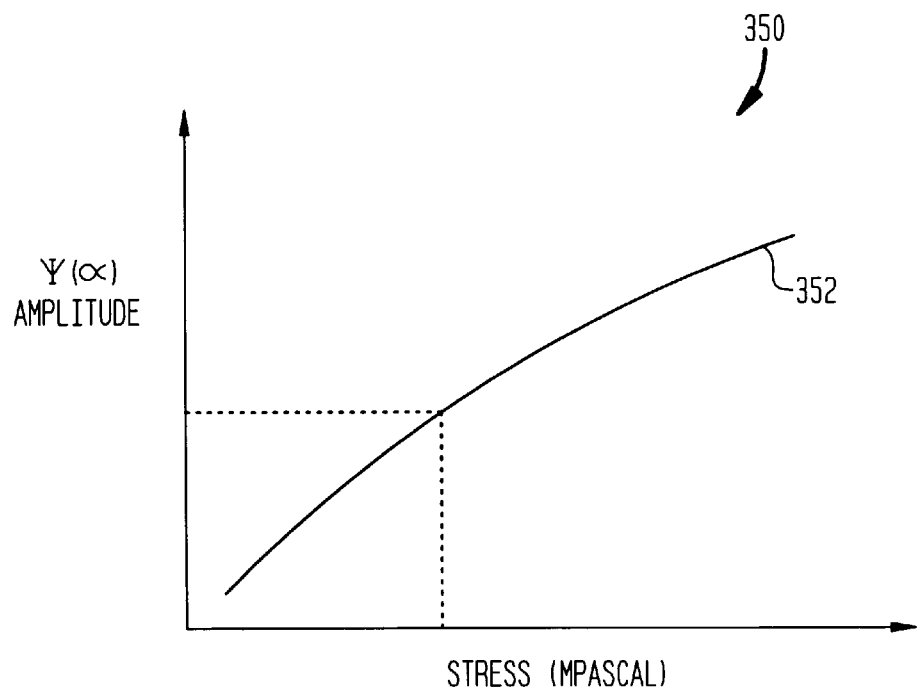
FIG. 3B illustrates, in accordance with the present invention, an exemplary calibration curve correlating a plurality of amplitudes between maximum and minimum ellipsometric parameter ψ to a plurality of stress values.

In accordance with one aspect of the present invention, the internal film stress is determined by first generating one or more calibration curves correlating a set of amplitudes to a set of stress values. FIGS. 3A and 3B illustrate exemplary calibration graphs 300 and 350 correlating a set of amplitudes between maximum and minimum ellipsometric parameters $\Delta(\alpha)$ and $\psi(\alpha)$, respectively, to a set of stress values. Graph 300 of FIG. 3A shows a curve 302 correlating a set of amplitudes between maximum and minimum ellipsometric parameter $\Delta(\alpha)$ to a set of stress values. On the other hand, Graph 350 depicts a curve 352 correlating a set of amplitudes between maximum and minimum ellipsometric parameter $\psi(\alpha)$ to a set of stress values.

As a first step in generating calibration curves 302 and 352, the conventional stress measurement methods can be applied on a bendable test sample to determine its stress value. For example, the aforementioned optical or electrical techniques can be used to measure the change in curvature of radius before and after depositing a film on the bendable test sample. The stress is then derived by using the well known Stoney's formula. Then, the revolving ellipsometry technique is applied to the bendable test sample to generate the curves of ellipsometric parameters $\Delta(\alpha)$ and $\psi(\alpha)$. In each of these curves, an amplitude between the maximum and minimum values is determined. The amplitudes for the curves correlate to the stress value evaluated in the initial step using the conventional stress measurement technique. Each of the amplitudes and the stress value evaluated define a single point in a calibration curve. The current embodiment of the present invention repeats this process for a set of bendable test samples characterized by different stress values to determine the calibration curves correlating a set of amplitudes for ellipsometric parameters $\Delta(\alpha)$ and $\psi(\alpha)$ to a set of stress values.

Figure 4:
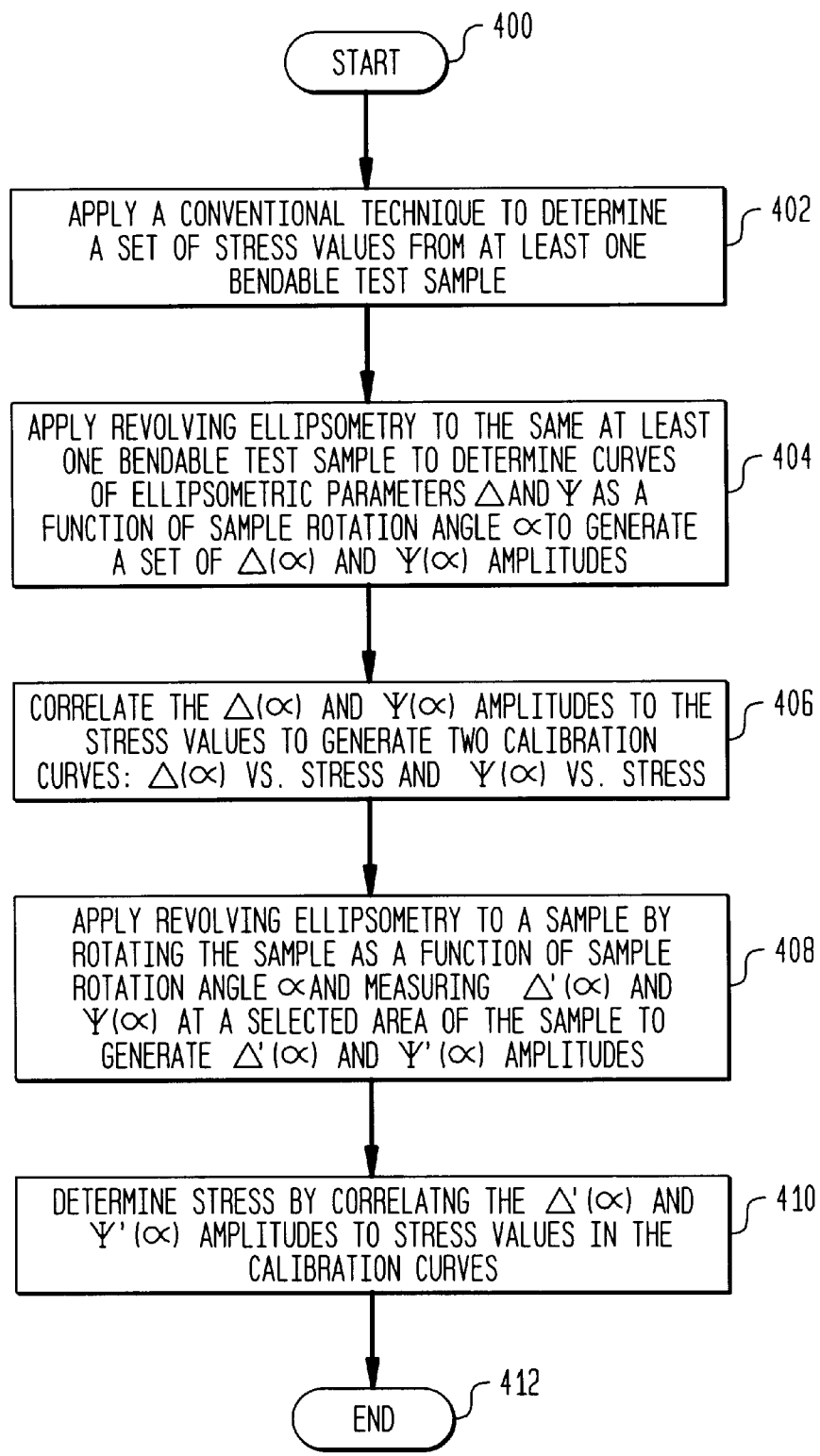
FIG. 4 illustrates the steps involved in determining stress on an isotropic sample using calibration curves correlating amplitude and stress in accordance with the present invention.

FIG. 4 illustrates, in accordance with the present invention, the steps involved in determining internal film stress in a sample using calibration curves correlating amplitudes and stress. In step 402, a conventional stress measurement technique is applied to at least one bendable test sample having different stress values to determine the stress on each of at least one bendable test sample. When more than one bendable test samples are used, the bendable test samples are preferably characterized by different stress values. Then in step 404, the revolving ellipsometry is applied to each of the bendable test samples to obtain the curves of ellipsometric parameters $\Delta(\alpha)$ and $\psi(\alpha)$ as a function of the sample rotation angle $\alpha$. In this step, one curve is generated for elllipsometric parameter $\Delta(\alpha)$ and another curve is generated for ellipsometric parameter $\psi(\alpha)$ for each of the stress values measured in step 402. The $\Delta(\alpha)$ and $\psi(\alpha)$ curves yield $\Delta(\alpha)$ amplitude and 104 ($\alpha$) amplitude, respectively, between the maximum and a minimum value in the respective curvesplotted as a function of rotating angle $\alpha$. Next in step 406, each of the $\Delta(\alpha)$ and $\psi(\alpha)$ amplitudes are correlated to the associated stress value to generate a calibration curve. One calibration curve is generated for each ellipsometric parameter $\Delta(\alpha)$ and $\psi(\alpha)$. Thus, two calibration curves correlating the amplitudes of $\Delta(\alpha)$ and $\psi(\alpha)$ to stress values can be generated.

In step 408, revolving ellipsometry is applied to an arbitrary sample for which stress measurement is desired in accordance with the present invention. The arbitrary sample may be any sample and includes unbendable, solid, and bendable samples. In this step, the ellipsometric parameters $\Delta'(\alpha)$ and $\psi'(\alpha)$ as a function of rotating angle $\alpha$ are measured at a selected area of the sample by rotating the sample. From the measured ellipsometric parameters $\Delta'(\alpha)$ and $\psi'(\alpha)$, the $\Delta'(\alpha)$ and $\psi'(\alpha)$ amplitudes between the maximum and minimum values for each ellipsometric parameters $\Delta'(\alpha)$ and $\psi'(\alpha)$ is determined. In one embodiment, the $\Delta'(\alpha)$ and $\psi'(\alpha)$ amplitudes may be determined by plotting the ellipsometric parameters $\Delta(')$ and $\psi(\alpha)$ as a function of the rotating angle $\alpha$.

Next in step 410, the $\Delta'(\alpha)$ and $\psi'(\alpha)$ amplitudes are used as indices to determine corresponding stress from the calibration curves generated in step 406. For example, the amplitude determined from ellipsometric parameter $\Delta'(\alpha)$ is used to determine the corresponding stress value from the calibration curve for the ellipsometric parameter $\Delta(\alpha)$. Likewise, the amplitude determined from ellipsometric parameter $\psi'(\alpha)$ is used to determine the corresponding stress value from the calibration curve for the ellipsometric parameter $\psi(\alpha)$. It should be appreciated that the calibration curves correlating the amplitudes of $\Delta(\alpha)$ and $\psi(\alpha)$ to stress values as obtained in steps 402, 404, and 406 need to be determined only once. After the calibration curves have been determined, all subsequent stress measurements on arbitrary samples can refer to these calibration curves to determine stress values. That is, once the calibraction curves have been generated, only steps 408 and 410 need to be performed to determine stress for an arbitrary sample.

The stress values obtained through $\Delta(\alpha)$ and $\psi(\alpha)$ calibration curves yield approximately the same stress value. In an ideal condition, the stress values would be identical. In a preferred embodiment, the stress values can be averaged out to obtain the final stress value. Since the stress values determined by measuring ellipsometric parameters $\Delta(\alpha)$ and $\psi(\alpha)$ are about the same, it should be appreciated that the stress value for a sample can be obtained by measuring only one ellipsometric parameter $\Delta(\alpha)$ or $\psi(\alpha)$. The process then terminates at step 412. It should be appreciated that internal stress can be determined on the basis of either or both ellipsometric parameters $\Delta$ or $\psi$. Accordingly, it is within the scope of the resent embodiment to determine internal stress on the basis of either or both ellipsometric parameters $\Delta$ or $\psi$.

In another embodiment of the present invention, the internal stress on a sample is determined quantitatively in accordance with equation $\tilde{n} = c\ s\ d$ where $\tilde{n}$ is a dielectric tensor, c is a stress optical coefficient of the sample, s is the internal stress to be determined, and d is the thickness of the sample at the selected area. For a sample with more than one film or material, $\tilde{n}$ is the effective dielectric tensor and d is the effective thickness taking into account all the films or materials in the sample. Based on this equation, the current embodiment of the present invention quantitatively determines the internal film stress on a sample by rotating the sample and measuring the ellipsometric angles $\Delta$ and $\psi$ as a function of a for a set of polarizer angles.

The quantitative stress measurement method of the present embodiment is based on the observation that internal stress typically induces optical anisotropy in a sample, which in turn affects the optical parameters of the system in a characteristic manner. This effect is often called stress-birefringence in crystal optics. For example, if an isotropic layer is subjected to stress in directions parallel to the interface, it becomes a phase plate with the optic axis being parallel to the surface of the layer. Specifically, the previous isotropic system described completely by a single complex refractive index (n+ik) now becomes optical anisotropic. To describe the optical properties of the optical anisotropic system, the previous isotropic optical parameters described by a complex number called complex refractive index n now become the aforementioned 3 by 3 complex dielectric tensor.

This complex dielectric tensor contains the stress optical parameters, i.e., the stress quantitatively. The present invention provides a method for determining this dielectric tensor which subsequently can be used to determine stress s by applying the aforementioned equation, $n = c\ s\ d$, where dielectric tensor n represents retardation measured in degrees, s represents the stress at a point in the sample, d is the thickness, and c is a constant called the stress optical coefficient. The stress optical coefficient c is dependent upon the material in the sample and can be found for the particular material in a tabulated form. Hence, stress can be determined at a point in the sample once the direction and the components of the dielectric tensor at different points of the sample are measured.

The dielectric tensor contains six components: $n_1$, $n_2$, $n_3$, $k_1$, $k_2$, and $k_3$. Accordingly, determination of the dielectric tensor $\tilde{n}$ requires measurement of 6 quantities. In most cases, when stress is applied, only two components of the dielectric tensor change. In particular, the extra-ordinary parameters $n_2$ and $k_2$ are same as $n_3$ and $k_3$, respectively. Hence, these cases can be characterized by four variables. In these situations, when the sample is rotated, the ellipsometry technique of the present invention can measure five values: $\Delta$, $\psi$, amplitude of $\Delta(\alpha)$, amplitude of $\psi(\alpha)$, and the phase difference between $\Delta(\alpha)$ and $\psi(\alpha)$. Accordingly, these five values can be used to determine dielectric tensor $\tilde{n}$, and thus the stress. Those skilled in the art will recognize that conventional ellipsometry technique can also be used to measure the thickness of the layer. The measurement of thickness d at the selected area of the sample using conventional ellipsometry technique or ellipsometer is well known in the art.

For more general cases where all components of the dielectric tensor $\tilde{n}$ differ, three independent ellipsometric measurements may be made. In these cases, the $\Delta(\alpha)$ and $\psi(\alpha)$ curves are measured for three different polarizer angles yielding three independent sets of $\Delta(\alpha)$ and $\psi(\alpha)$ curves (15 parameters) which now can be used to determine the dielectric tensor using well known conventional least square fit procedures.

Figure 5:
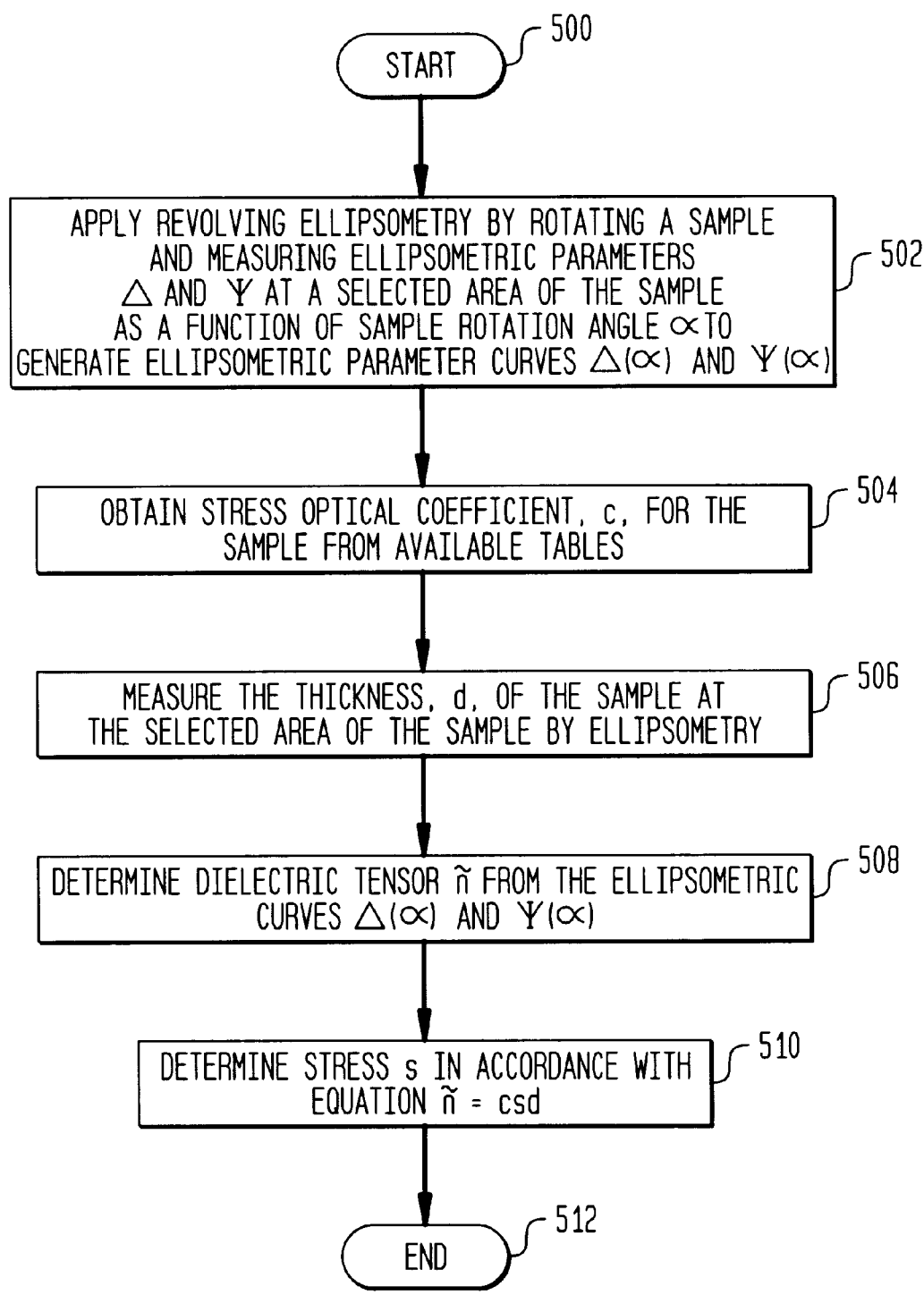
FIG. 5 illustrates, in accordance with the present invention, the steps involved in determining internal film stress on a sample under stress by rotating a sample.

FIG. 5 illustrates the steps involved in determining the internal film stress on an arbitrary sample by rotating a sample. In step 502, revolving ellipsometry is applied to the sample by rotating the sample as a function of rotation angle $\alpha$ and measuring ellipsometric parameters $\Delta$ and $\psi$ at a selected area of the sample to generate ellipsometric parameter curves $\Delta(\alpha)$ and $\psi(\alpha)$. Then in step 504, the stress optical coefficient, c, which is a tensor for the particular material comprising the sample is obtained from a well known table of such values such as Handbook of Chemistry and Physics, CRC, Weast (1996). In step 506, the thickness, d, at the selected area of the sample is measured through ellipsometry, which can be either the conventional non-revolving ellipsometry or the revolving ellipsometry in accordance with the present invention. Then in step 508, the dielectric tensor $\tilde{n}$ is determined from the measured ellipsometric parameter curves $\Delta(\alpha)$ and $\psi(\alpha)$, preferably through a fit procedure such as least fit procedure utilizing the measured data. Next in step 510, using the dielectric tensor $\tilde{n}$ obtained in step 508, the values $\tilde{n}$, c, and d are used to determine the value of stress, s, in accordance with the well known equation, $\tilde{n}=c\,s\,d$. Given values $\tilde{n}$, c, and d, those skilled in the art will appreciate that this equation can readily be solved for stress through well known inversion or fit procedure. The process then terminates in step 512. In the present invention, it should be appreciated that the ellipsometric parameters $\Delta$ and $\psi$ may be measured for a set of light wavelengths to implement spectroscopic revolving ellipsometry.

Figure 6:
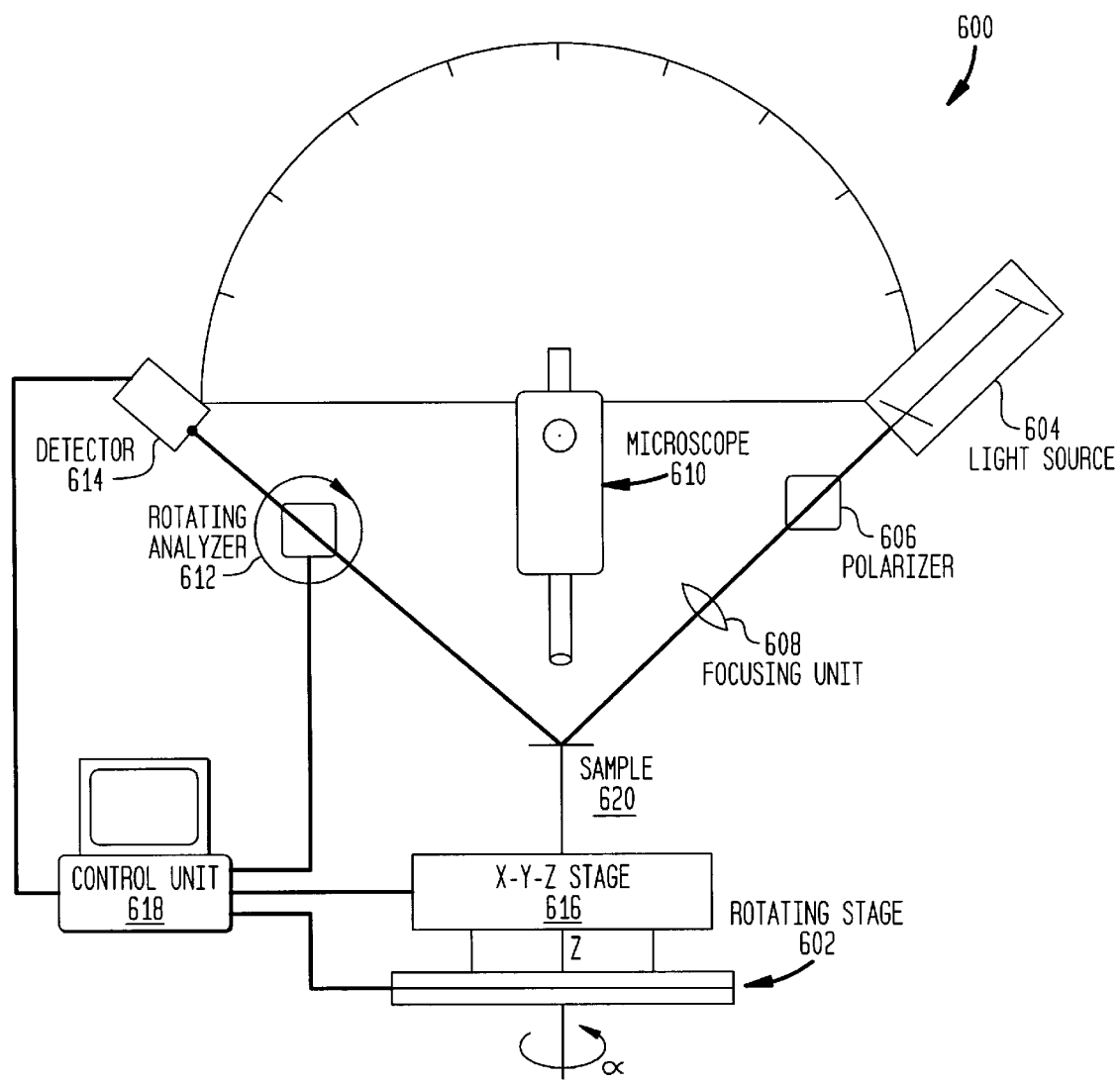
FIG. 6 provides an apparatus for measuring internal film stress on a sample under stress at high lateral resolutions in accordance with the present invention.

In accordance with yet another embodiment of the present invention, FIG. 6 provides an apparatus 600 for measuring internal film stress on a sample 620 at high lateral resolutions. The apparatus 600 comprises an ellipsometer and a rotating stage 602. The rotating stage 602 is rotatably disposed below the ellipsometer for rotating the sample to vary the angle of rotation a around a center of rotation axis. The ellipsometer measures ellipsometric parameters $\Delta$ and $\psi$ by directing a linearly polarized incident light onto a selected area of sample 620 to generate an elliptically polarized reflected light. The ellipsometer compares the linearly polarized incident light and said elliptically polarized reflected light to measure the ellipsometric $\Delta$ and $\psi$ values. In contrast to conventional ellipsometers, apparatus 600 can measure ellipsometric parameter $\Delta(\alpha)$ and $\psi(\alpha)$ curves as a function of sample rotating angle $\alpha$.

The ellipsometer comprises a light source 604, a polarizer 606, a focusing unit 608, an x-y-z stage 616, a microscope 610, a rotating analyzer 612, a detector, and a control unit 618. Light source 604 generates an incident light such as a laser beam, a light beam, or any type of light. In particular, a light source which can be tuned in wavelength can be used to implement a spectroscopic method. In one embodiment, a polychromatic light source can be used in combination with a monochromator or diode-detector array in oder to allow spectroscopic measurements.

Polarizer 606 receives the incident light and linearly polarizes the incident light. Focusing unit 608 receives the light and focuses the linearly polarized light to provide and resolve high lateral resolutions on the surface of sample 620. Focusing unit 608 may include a lens or a lense system such as a microscope objective. Sample 620 is disposed on x-y-z stage, which changes the position of sample 620 in x, y, and z directions. Microscope 610 is aligned to the center of rotation of the rotating stage 602 for selecting an area of sample 620 to determine internal film stress.

With reference to FIG. 6, the focused and linearly polarized incident light is directed to the selected area of sample 620 and is then reflected off sample 620 to generate elliptically polarized reflected light. Rotating analyzer 612 receives the elliptically polarized reflected light and transforms the polarization state to an intensity change. Analysis of this intensity signal allows determination of ellipsometric parameters $\Delta$ and $\psi$. Detector 614 receives the reflected light through rotating analyzer and detects the light intensities to generate ellipsometric parameters $\Delta$ and $\psi$ in terms of light intensity. Control unit 618 is coupled to detector 614, rotating analyzer 612, z-y-z stage 616, and rotating stage 602 for coordinating these units. Control unit 618 receives and correlates the ellipsometric parameters $\Delta$ and $\psi$ from detector 614 to the angle of rotation, $\alpha$, to determine stress at the selected area of sample 620.

The configuration of apparatus 600 allows selection of an arbitrary position on sample 620 (i.e., mapping) and to rotate it without affecting the ellipsometric alignment. In addition, the angle of incidence and the polarizer angle are adjustable. By thus rotating the sample under the ellipsometer, apparatus 600 allows measurement of ellipsometric parameters $\Delta$ and $\psi$, and ellipsometric parameter curves $\Delta(\alpha)$ and $\psi(\alpha)$ for determining stress on sample 620 by using the techniques described above. In one embodiment, the ellipsometric parameters $\Delta$ and $\psi$ may be measured for a set of light wavelengths to implement spectroscopic revolving ellipsometry.

In contrast to the conventional stress measurement techniques, the present invention provides several important advantages. For example, the methods and apparatus of the present invention can evaluate stress on any sample such as unbendable, i.e., solid, samples. Further, the stress evaluation of the present invention are neither destructive nor invasive since samples are not physically bent. Additionally, the present methods and apparatus can be applied on patterned materials with sensitive geometry. Also, anisotropic samples can be tested for internal stress. Furthermore, the present invention can determine stress on microscopic structures at high lateral resolutions.

MATHEMATICAL DISCUSSION

In this section, a detailed mathematical description of the above methods is presented. To facilitate ease of understanding, this section provides background mathematical analysis in deriving the aforementioned dielectric tensor, n, from ellipsometric parameters $\Delta(\alpha)$ and $\psi(\alpha)$ and their curves. Similar discussion may be found in A. Michaelis and J. W. Schultze, *Thin Solid Films* 274 (1996) 82–94.

In order to derive the dielectric tensor (or permittivity tensor), the coefficients of the 2×2 scattering matrix $\underline{S}_{Aniso}$ which describes the optical properties of any medium under investigation, have to be determined.

$$\begin{pmatrix} E_{ref,p} \\ E_{ref,s} \end{pmatrix} = \underline{S}_{Aniso} \begin{pmatrix} E_{in,p} \\ E_{in,s} \end{pmatrix} \tag{2}$$

E, H, D, B denote the electromagnetic field vectors as usual. The indices (ref) and (in) refer to incident and reflected light polarized parallel (p) and perpendicular (s) to the plane of incidence. To be complete the whole formalism starting from Maxwell's curl equations in 6×6 matrix form shall be given here. The notation and sign conventions of Berreman and De Smet are used (see e.g., D. W. Berreman and T. J. Scheffer, *Phys. Rev. Lett.*, 25 (1970) 577; D. W. Berreman, *J. Opt. Soc. Am*, 62 (1972) 502; D. W. Berreman, *J. Opt. Soc. Am.*, 63 (1973) 1374; D. J. De Smet, *Surf. Sci.*, 56 (1976) 293; and R. M. A. Azzam and N. M. Bashara, *Ellipsometry and Polarized Light*, 3rd Ed., North Holland, Amsterdam, 1992, all of which are incorporated herein by reference):

$$\begin{pmatrix} 0 & 0 & 0 & 0 & -\frac{\delta}{\delta y} & \frac{\delta}{\delta y} \\ 0 & 0 & 0 & \frac{\delta}{\delta x} & 0 & -\frac{\delta}{\delta x} \\ 0 & 0 & 0 & -\frac{\delta}{\delta y} & \frac{\delta}{\delta x} & 0 \\ 0 & \frac{\delta}{\delta z} & -\frac{\delta}{\delta y} & 0 & 0 & 0 \\ -\frac{\delta}{\delta z} & 0 & \frac{\delta}{\delta x} & 0 & 0 & 0 \\ \frac{\delta}{\delta y} & -\frac{\delta}{\delta x} & 0 & 0 & 0 & 0 \end{pmatrix} \begin{pmatrix} E_x \\ E_y \\ E_z \\ H_x \\ H_y \\ H_z \end{pmatrix} = i\omega \begin{pmatrix} D_x \\ D_y \\ D_z \\ B_x \\ B_y \\ B_z \end{pmatrix} \tag{3}$$

This can be written in short form as:

$$\underline{O}G = i\omega C \tag{4}$$

The general material equations which describe the correlation between E, H, and D, B can be put as:

$$C = \underline{M}G = \begin{bmatrix} \underline{\varepsilon} & \underline{\sigma} \\ \underline{\sigma} & \underline{\mu} \end{bmatrix} G \tag{5}$$

Here the quantity M denotes the 6×6 optical matrix consisting of the permittivity tensor $\underline{\varepsilon}$, the permeability tensor $\underline{\mu}$, and the optical rotation tensors $\underline{\sigma}$. In this context, only the permittivity tensor $\underline{\varepsilon}$ is important, i.e. the assumption $\underline{\mu}=1$ and $\underline{\sigma}=0$ is used. Combining Eqs. (4) and (5) and assuming the properties of the medium to be time independent yields:

$$\underline{O}G = i\omega \underline{M} G \tag{6}$$

or $$\underline{O}\Gamma = i\omega \underline{M} \Gamma \tag{7}$$

if the spatial part of the plane wave solution $\Gamma = G \exp(-i\omega t)$ is considered only.

Figure 7A:
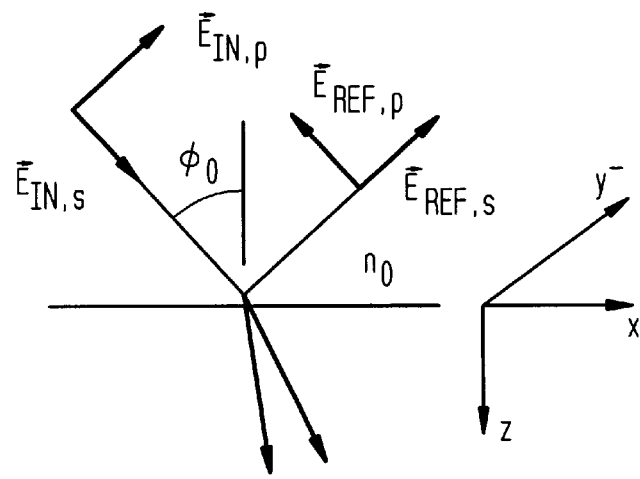
FIG. 7A illustrates reflection and transmission of light at an interface between an isotropic medium (refractive index $n_1$) and an anisotropic medium of bare substrate.
Figure 7B:
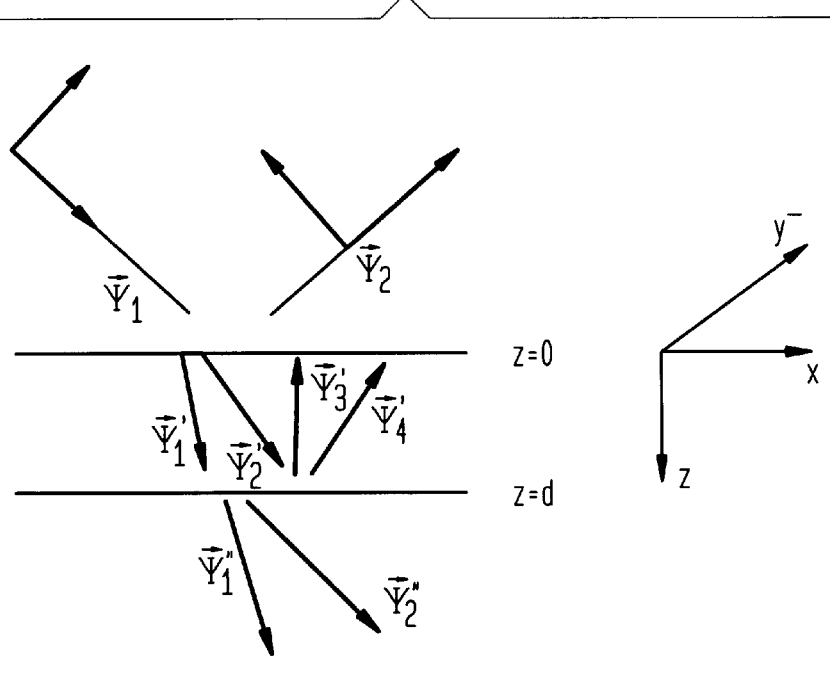
FIG. 7B illustrates reflection and transmission of light at an interface between an isotropic medium (refractive index $n_1$) and an anisotropic medium of layered substrate.

Now a particular case is considered, where the light incident from some external isotropic medium (air or liquid) with a refractive index $n_i$ hits a general anisotropic system at an angle of incidence $\phi$. The coordinate system shown in FIGS. 7A and 7B is chosen in a way that the propagation vector of light lies in the x-z plane and the interface between the two media is the x-y plane, i.e.

$$\frac{\delta}{\delta y} \Gamma = 0.$$

The boundary conditions for the tangential fields cause a spatial dependence of the x component of the propagation vector $\chi$ on the x direction as e' leading to the generalized Snell's law:

$$\chi = \tilde{n}_i(\omega/c) \sin \phi_i \tag{8}$$

where c is the velocity of light, $\phi_i$ denotes the refractive angle of the medium i. The correlation between the complex permittivity number $\varepsilon$ and the complex refractive index $\tilde{n}$ is given by $$\tilde{n}^2(\omega) = n^2 + k^2 2 + i n k = \varepsilon(\omega) \tag{9}$$

where n is the index of refraction and k the extinction coefficient.

For geometric reasons the curl operator simplifies to $$\nabla X = \begin{bmatrix} 0 & -\delta/\delta x & 0 \\ \delta/\delta z & 0 & i_\chi \\ 0 & -i_\chi & 0 \end{bmatrix} \tag{10}$$

Using this operator, the six differential equations given by Eq. (7) can be reduced to four linear differential equations by eliminating $E_z$ and $H_z$ which depend linearly on the other components. The resulting equation can be written as:

$$\frac{\delta}{\delta z} \begin{pmatrix} E_x \\ H_y \\ E_y \\ -H_x \end{pmatrix} = \underline{\Delta} \begin{pmatrix} E_x \\ H_y \\ E_y \\ -H_x \end{pmatrix} \tag{11}$$

The elements of the 4×4 matrix $\underline{\Delta}$ can be computed from the elements of the optical matrix $\underline{M}$.

Figure 8:
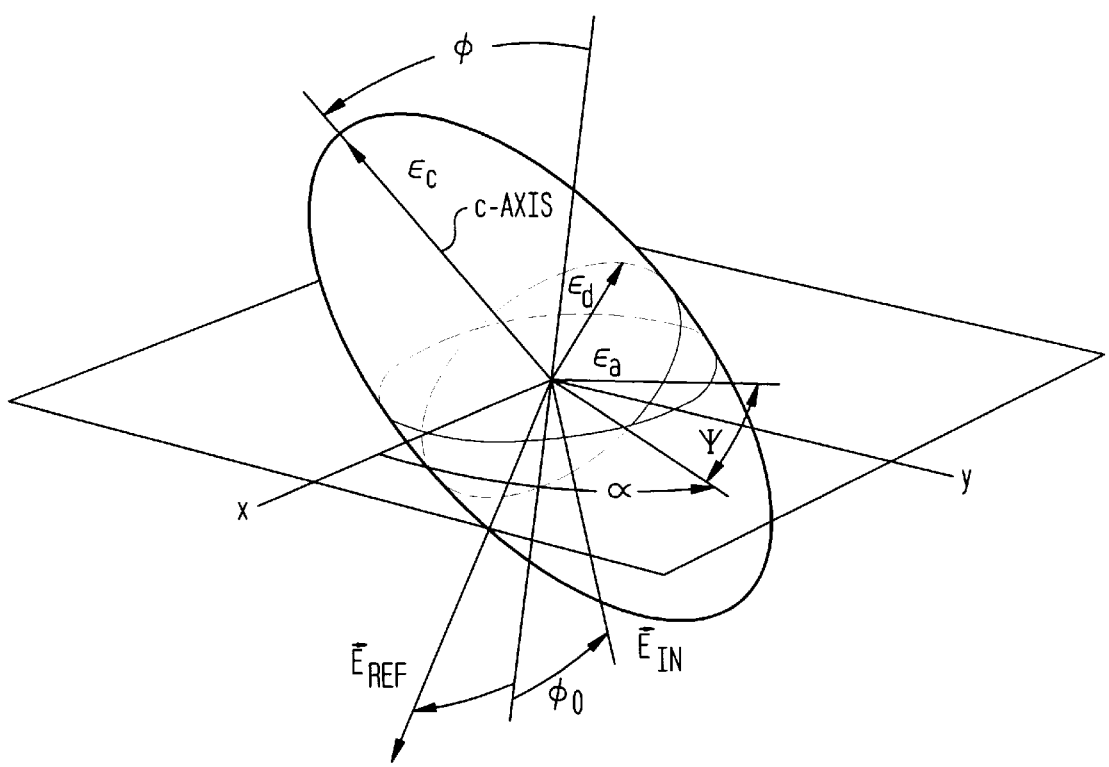
FIG. 8 illustrates Euler angles α, φ, and ψ of the dielectric tensor with respect to the sample surface (x,y) plane and the normal (z) with the $\epsilon_z$ component corresponding to the optical axis (c axis).

Any anisotropic medium can be described by the tensor components of its permittivity ellipsoid $\varepsilon_a$, $\varepsilon_b$, and $\varepsilon_c$ in its main axis system as (see FIG. 8):

$$\underline{\varepsilon} = \begin{bmatrix} \varepsilon_a & 0 & 0 \\ 0 & \varepsilon_b & 0 \\ 0 & 0 & \varepsilon_c \end{bmatrix} \quad (12)$$

The first step to calculate $\underline{\Delta}$ is to transfer the tensor $\underline{\varepsilon}$ into the coordinate system of the matrix $\underline{\Delta}$ (ellipsometric coordinate system). For this, the tensor must be rotated around the Euler angles $\alpha$, $\phi$ and $\psi$ as follows:

$$\underline{\varepsilon}_{new} = \underline{C}(\psi)\underline{B}(\phi)\underline{A}(\alpha) \times \underline{\varepsilon}_{old} \times \underline{A}(\alpha)\underline{B}(-\phi)\underline{C}(-\psi) \quad (13)$$

with the Euler matrices $$\underline{A}(\alpha) = \begin{pmatrix} \cos\alpha & -\sin\alpha & 0 \\ \sin\alpha & \cos\alpha & 0 \\ 0 & 0 & 1 \end{pmatrix} \quad (14)$$

$$\underline{B}(\varphi) = \begin{pmatrix} 1 & 0 & 0 \\ 0 & \cos\varphi & -\sin\varphi \\ 0 & \sin\varphi & \cos\varphi \end{pmatrix}$$

$$\underline{C}(\psi) = \begin{pmatrix} \cos\psi & -\sin\psi & 0 \\ \sin\psi & \cos\psi & 0 \\ 0 & 0 & 1 \end{pmatrix}$$

By it, the components of the matrix $$\underline{\Delta} = \begin{pmatrix} \Delta_{11} & \Delta_{12} & \Delta_{13} & 0 \\ \Delta_{21} & \Delta_{11} & \Delta_{23} & 0 \\ 0 & 0 & 0 & \Delta_{34} \\ \Delta_{23} & \Delta_{13} & \Delta_{43} & 0 \end{pmatrix} \quad (15)$$

can be calculated to:

$$\Delta_{13} = -X(\varepsilon_{13}\cos\phi - \varepsilon_{23}\sin\phi)/\varepsilon_{33} \quad (16)$$

$$\Delta_{13} = -X(\varepsilon_{13}\sin\phi - \varepsilon_{23}\cos\phi)/\varepsilon_{33}$$

$$\Delta_{12} = 1 - X^2/\varepsilon_{33}$$

$$\Delta_{21} = \left[\left(\frac{\varepsilon_{11}-\varepsilon_{22}}{2} - \frac{\varepsilon_{13}^2 - \varepsilon_{23}^2}{2\varepsilon_{33}}\right)\cos 2\varphi - \left(\varepsilon_{12} - \frac{\varepsilon_{13}\varepsilon_{23}}{\varepsilon_{33}}\right)\sin 2\varphi\right] + \left(\frac{\varepsilon_{11}+\varepsilon_{22}}{2} - \frac{\varepsilon_{13}^2 + \varepsilon_{23}^2}{2\varepsilon_{33}}\right)$$

$$\Delta_{43} = -\left[\left(\frac{\varepsilon_{11}-\varepsilon_{22}}{2} - \frac{\varepsilon_{13}^2 - \varepsilon_{23}^2}{2\varepsilon_{33}}\right)\cos 2\varphi - \left(\varepsilon_{12} - \frac{\varepsilon_{13}\varepsilon_{23}}{\varepsilon_{33}}\right)\sin 2\varphi\right] + \left(\frac{\varepsilon_{11}+\varepsilon_{22}}{2} - \frac{\varepsilon_{13}^2 + \varepsilon_{23}^2}{2\varepsilon_{33}}\right) - X^2$$

$$\Delta_{23} = \left[\left(\frac{\varepsilon_{11}-\varepsilon_{22}}{2} - \frac{\varepsilon_{13}^2 - \varepsilon_{23}^2}{2\varepsilon_{33}}\right)\sin 2\varphi - \left(\varepsilon_{12} - \frac{\varepsilon_{13}\varepsilon_{23}}{\varepsilon_{33}}\right)\cos 2\varphi\right]$$

$$\Delta_{34} = 1$$

using the definitions:

$$\varepsilon_{11} = \varepsilon_a \cos^2\psi + \varepsilon_b \sin^2\psi \quad (17)$$

$$\varepsilon_{12} = (\varepsilon_a - \varepsilon_b)\sin\psi\cos\psi\cos\alpha$$

$$\varepsilon_{13} = (\varepsilon_a - \varepsilon_b)\sin\psi\cos\psi\sin\alpha$$

$$\varepsilon_{22} = (\varepsilon_a \sin^2\psi + \varepsilon_b \cos^2\psi)\cos^2\alpha + \varepsilon_c \sin^2\alpha$$

$$\varepsilon_{23} = (\varepsilon_a \sin^2\psi + \varepsilon_b \cos^2\psi - \varepsilon_c)\cos\alpha\sin\alpha$$

$$\varepsilon_{33} = (\varepsilon_a \sin^2\psi + \varepsilon_b \cos^2\psi)\sin^2\alpha + \varepsilon_c \cos^2\alpha$$

Here X means the non-dimensional relation of the x component of the propagation vector to the wave number $v = \omega/c$. For the geometry of FIG. 8, it results in $X = \sin\phi_0$.

Using the ansatz of monochromatic, linear polarized, plane light waves:

$$\Psi(z) = \Psi(0)e^{iqz} \text{ with } \Psi = \begin{pmatrix} E_x \\ H_y \\ E_y \\ -H_x \end{pmatrix} \quad (18)$$

in the generalized wave Eq. (11) yields the eigenvalue equation as follows:

$$[\omega[\underline{\Delta} - q\underline{I}]]\Psi(0) = 0 \quad (19)$$

$\underline{I}$ is the 4×4 identity matrix. This equation has got four eigenvalues q and four associated eigen-vectors $\Psi$. Each q represents the z component of a propagation vector, the associated vectors $\Psi$ describe the state of polarization of the light beams. If the solutions for the q values are real, then two values will be positive and two will be negative. In the case where light is incident on a homogeneous anisotropic medium (two-phase model), only the positive values have physical relevance. If, on the other hand, light is reflected back from a second interface (three- and more-phase models), then the back reflexes are described by the negative q values.

The situation is similar for complex solutions of the q values. Now the q values with a positive imaginary part represent light beams traveling in the +z direction, the other two values represent light reflected in the -z direction.

In the case shown in FIG. 7A (two-phase model, no layer), the boundary conditions of the x and y components of the E and H fields lead to the four equations:

$$\Psi_1 + \Psi_2 = A\Psi_1'(0) + B\Psi_2'(0) + C\Psi_3'(0) + D\Psi_4'(0) \quad (20)$$

where $\Psi'$ are the eigen-vectors of the in +z direction propagating waves, A and B are constants of proportionality. The $\Psi$ vectors contain the x and y components of E and H for the incident and reflected light, respectively:

$$\Psi_1 = \begin{pmatrix} E_{in,p}\cos\phi \\ \tilde{n}_{in}E_{in,p} \\ E_{in,s} \\ \tilde{n}_{in}E_{in,s}\cos\phi \end{pmatrix} \quad \Psi_2 = \begin{pmatrix} E_{ref,p}\cos\phi \\ \tilde{n}_{in}E_{ref,p} \\ E_{ref,s} \\ \tilde{n}_{in}E_{ref,s}\cos\phi \end{pmatrix} \quad (21)$$

By eliminating A and B and rearranging the resulting equation, and equation identical to Eq. (2)

$$\begin{pmatrix} E_{ref,p} \\ E_{ref,s} \end{pmatrix} = \underline{S}_{Aniso} \begin{pmatrix} E_{in,p} \\ E_{in,s} \end{pmatrix} \quad (22)$$

can be obtained, from which the scattering matrix $\underline{S}_{Aniso}$ can be determined.

In the case of a film-covered sample (three-phase model, film thickness d) as shown in FIG. 7B, a similar solution can be found. For any medium it is possible to construct a matrix $\underline{P}(d)$ with the property $$\underline{P}(d) \cdot \Psi(0) = \Psi(d) \quad (23)$$

P(d) can be constructed as follows. First, a 4×4 matrix $\underline{\psi}$ using the $\Psi$ vectors as columns is constructed. Another 4×4 matrix $\underline{K}(d)$ is constructed by setting the off-diagonal elements to zero and the diagonal elements to $$\underline{K}_{jj}(d) = \exp(iq_j d) \tag{24}$$

where the q values are arranged in the same order as the $\Psi$. This yields $$\underline{P}(d) = \underline{\psi}\underline{K}(d)\underline{\psi}^{-1} \tag{25}$$

Now, boundary conditions at two interfaces must be matched $$\Psi_1 + \Psi_2 = A\Psi_1'(0) + B\Psi_2'(0) + C\Psi_3'(0) + D\Psi_4'(0) \tag{26}$$

$$E\Psi_1'' + F\Psi_2'' = A\Psi_1'(d) + B\Psi_2'(d) + C\Psi_3'(d) + D\Psi_4'(d)$$

where A . . . F are constants of proportionality. With Eq. (23) it follows that $\underline{P}(d) \cdot A \cdot \Psi_1'(0) = A \cdot \Psi_1'(d)$ and so on, i.e.

$$\underline{P}(d)(\Psi_1 + \Psi_2) = E\Psi_1' + F\Psi_2' \tag{27}$$

This equation is formally identical to Q. (20), i.e. that scattering matrix can be determined in this case, too. The formalism can be extended for the description of any multilayer system.

The relation between the elements of the scattering matrix and the ellipsometrically measured angles $\Delta$ and $\Psi$ which describe the polarization state of the reflected light is given by $$\tan\psi \cdot e^{i\Delta} = \frac{S_{21p}}{S_{11p}} \cdot \frac{S_{11s}}{S_{21s}} \tag{28}$$

By a fit procedure layer thicknesses and anisotropic optical constants, e.g., the dielectric tensor, as well as the Euler angles which describe the orientation of the optical axis can now be determined.

As an example for the application of this formalism, the effect of the crystallographic anisotropy of Titanium-material (Ti) on ellipsometry is discussed below. Ti crystallizes in a hcp lattice and therefore is optical birefringent. The optical properties are therefore described by its permittivity tensor $$\underline{\varepsilon} = \begin{bmatrix} \varepsilon_{a0} & 0 & 0 \\ 0 & \varepsilon_{a0} & 0 \\ 0 & 0 & \varepsilon_0 \end{bmatrix} \tag{1}$$

where the index (ao) denotes the extraordinary and (o) the ordinary ray. The orientation of the optical axis coincides with $\varepsilon_o$. The crystalline $TiO_2$ modifications rutile (optical positive, i.e. $n_{ao} > n_o$) and anatase (optical negative, $n_{ao} < n_o$) are birefringent, too. Both modifications belong to the tetragonal crystal system.

Figure 9A:
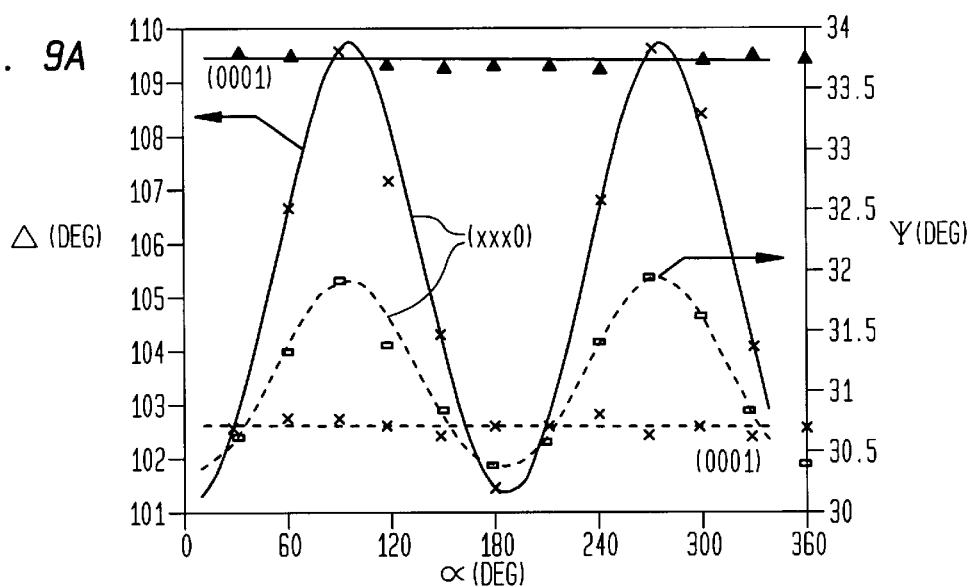
FIG. 9A illustrates application of a related method involving anisotropy ellipsometry on (0001) and (xxx0) surfaces of anisotropic samples for determination of crystallographic orientation.
Figure 9B:
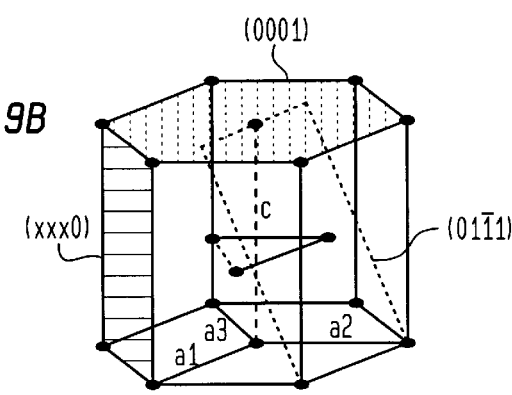
FIG. 9B illustrates a Ti Bravais lattice where Ti surfaces were layered by potentiodynamically formed (50 mV s$^{-1}$) 4 V TiO$_2$ layers (0.5 M H$_2$SO$_4$) with c denoting an optical axis.
Figure 9C:
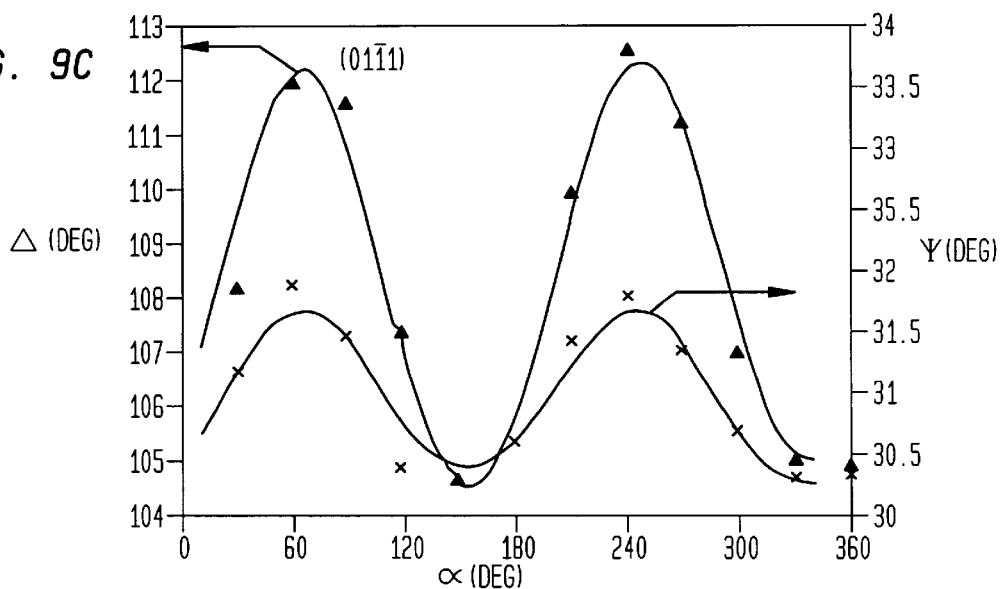
FIG. 9C illustrates anisotropy ellipsometry on (01$\bar{1}$1) surface.

In FIGS. 9A, 9B, and 9C, experimental anisotropy ellipsometry data for three different orientations of the Ti substrate's optical axis with respect to the ellipsometric plane of incidence are shown to give a first suggestion. The measurements were carried out on Ti single crystals of known orientation (Laue method). In this particular case the surfaces were covered by potentiodynamically formed $TiO_2$ layers of about 8 nm thickness. The (0001) orientation has its c axis parallel to the plane of incidence, (xxx0) denotes any surface with an orientation of the c axis perpendicular to the plane of incidence. The Ti unit cell with the different crystal surfaces is also shown in FIGS. 9A, 9B, and 9C. The anisotropy causes a strong variation of the ellipsometric $\Delta$ and $\Psi$ values in dependence on sample rotation around the surface normal. The quantity $\alpha$ with arbitrary zero denotes the size of sample rotation. The symbols in FIG. 9 refer to the revolving ellipsometric measurements whereas the solid lines or curves show the result of a fit-procedure calculation using a Marquard least square fit-procedure according to the mathematical formalism described above yielding the components and orientation of the dielectric tensor $\bar{n}$. The close fit of the curves and the experimental data confirms the formalism. Analogous calculations may be performed to determine the dielectric tensor in case of samples under stress.

While this invention has been described in terms of several preferred embodiments, there are alterations, permutations, and equivalents which fall within the scope of this invention. It should also be noted that there are many alternative ways of implementing the methods and apparatus of the present invention. It is therefore intended that the following appended claims be interpreted as including all such alterations, permutations, and equivalents as falling within the true spirit and scope of the present invention.

I claim:

1. A method for determining internal stress in a sample at high lateral resolution, said sample comprising at least one material and having a planar or smooth surface, said method comprising:

generating a calibration curve correlating a set of first ellipsometric amplitudes to a set of first stress values, one first stress value for each first ellipsometric amplitude;

measuring a second ellipsometric parameter over a range of rotation angle $\alpha$ at a selected area of the sample by rotating the sample to determine a second ellipsometric amplitude; and determining the internal stress at the selected area of the sample from the calibration curve by using the second ellipsometric amplitude as an index to determine a corresponding first stress value from the calibration curve.

2. The method as recited in claim 1 wherein the calibration curve is generated from at least one bendable test sample, the bendable test sample comprising at least one material and characterized by at least one first stress value.

3. A method for determining internal stress in a sample at high lateral resolution, said sample comprising at least one material and having a planar or smooth surface, said method comprising:

generating a calibration curve correlating a set of first ellipsometric amplitudes to a set of first stress values, one first stress value for each first ellipsometric amplitude, wherein the calibration curve is generated from at least one bendable test sample, the bendable test sample comprising at least one material and characterized by at least one first stress value, the step further comprising;

measuring the set of first stress values in said at least one bendable test sample;

measuring, for each first stress value, a first ellipsometric parameter over the range of the rotation angle $\alpha$ by rotating said at least one bendable test sample to generate a set of first ellipsometric parameter values;

determining, for each set of the first ellipsometric parameter values, the first ellipsometric amplitude representing the difference between a first maximum and a first minimum values defined by the set of first ellipsometric parameter values; and correlating the first ellipsometric amplitudes to the first stress values to generate the calibration curve, measuring a second ellipsometric parameter over a range of rotation angle α at a selected area of the sample by rotating the sample to determine a second ellipsometric amplitude; and determining the internal stress at the selected area of the sample from the calibration curve by using the second ellipsometric amplitude as an index to determine a corresponding first stress value from the calibration curve.

4. The method as recited in claim 3 wherein a set of second ellipsometric parameter values is generated from the second ellipsometric parameter measured over the range of the rotation angle α of the sample.

5. The method as recited in claim 4 wherein the set of second ellipsometric parameter values defines a second ellipsometric parameter curve, wherein the second ellipsometric amplitude is the difference between a second maximum and a second minimum values in the second ellipsometric parameter curve.

6. The method as recited in claim 4 wherein the second ellipsometric amplitude is the difference between second maximum and second minimum values defined by the set of second ellipsometric parameter values.

7. The method as recited in claim 3 wherein the first ellipsometric parameter and the second ellipsometric parameter are both Δ.

8. An apparatus for measuring internal film stress on an anisotropic sample at a high lateral resolution, said anisotropic sample comprising at least one layer of a first material disposed on a second material, said apparatus comprising:

an ellipsometer for measuring ellipsometric parameters Δ and ψ, said ellipsometer directing a linearly polarized incident light onto a selected area of said sample to generate an elliptically polarized reflected light, said ellipsometer comparing said linearly polarized incident light and said elliptically polarized reflected light to measure said ellipsometric parameters Δ and ψ; and a rotating stage rotatably disposed below said ellipsometer for rotating said sample so as to vary an angle of rotation α about a center of rotation axis, said center of rotation axis being aligned with said ellipsometer wherein said ellipsometer correlates said ellipsometric parameters Δ and ψ to said angle of rotation α to determine the internal film stress at said selected area of said sample at a high lateral resolution.

9. The method as recited in claim 3 wherein the first ellipsometric parameter and the second ellipsometric parameter are both ψ.

10. The method as recited in claim 3 wherein the first ellipsometric parameter and the second ellipsometric parameter are measured over the rotation angle α.

11. The method as recited in claim 7 wherein the first ellipsometric parameter Δ and the first ellipsometric parameter ψ are measured as a function of the rotation angle α to generate the set of first ellipsometric parameter values Δ(α).

12. The method as recited in claim 9 wherein the first and second ellipsometric parameter ψ is measured as the function of the rotation angle α to generate the set of first ellipsometric parameter values ψ(α).

13. The method as recited in claim 6 wherein both the first ellipsometric parameter and the second ellipsometric parameter further comprise an ellipsometric parameter Δ and an ellipsometric parameter ψ.

14. The method as recited in claim 13 wherein the calibration curve comprises a first calibration curve and a second calibration curve.

15. The method as recited in claim 14 wherein the first calibration curve is generated for the first ellipsometric parameter Δ and the second calibration curve is generated for the first ellipsometric parameter ψ.

16. The method as recited in claim 13 wherein the ellipsometric parameters Δ and ψ are measured over the rotation angle α.

17. The method as recited in claim 13 wherein the ellipsometric parameters Δ and ψ are measured over the rotation angle α to generate the set of first and second ellipsometric parameter values Δ(α) and ψ(α), respectively.

18. The method as recited in claim 17 wherein the second amplitude further comprises Δ(α) amplitude and ψ(α) amplitude.

19. The method as recited in claim 17 wherein Δ(α) amplitude and ψ(α) amplitude of the second amplitude are used as an index to the first calibration curve and the second calibration curve, respectively, to determine the corresponding stress values.

20. The method as recited in claim 19 wherein the stress values corresponding to Δ(α) amplitude and ψ(α) amplitude of the second amplitude are averaged to determine the internal stress.

21. The method as recited in claim 1 wherein the second ellipsometric parameters are measured at the high lateral resolution by focusing a linearly polarized incident light onto the selected area of the sample to generate an elliptically polarized reflected light and then measuring the second ellipsometric parameters of the elliptically polarized reflected light.

22. The method as recited in claim 1 wherein the sample is a solid sample.

23. The method as recited in claim 1 wherein the sample is not bent.

24. The method as recited in claim 1 wherein said sample is an integrated circuit device.

25. A method for determining internal stress in a sample at high lateral resolution, said sample comprising at least one material and having a planar or smooth surface, said method comprising:

generating a pair of Δ(α) and ψ(α) calibration curves correlating first ellipsometric Δ(α) and ψ(α) amplitudes to a set of first stress values;

measuring a pair of second ellipsometric parameters Δ and ψ over a range of rotation angle α at a selected area of the sample by rotating the sample to determine a second ellipsometric Δ'(α) and ψ'(α) amplitudes; and determining the internal stress at the selected area of the sample from the pair of Δ(α) and ψ(α) calibration curves by using the second ellipsometric Δ'(α) and ψ'(α) amplitudes as indices to determine corresponding first stress values from the pair of Δ(α) and ψ(α) calibration curves.

26. The method as recited in claim 25 wherein the corresponding first stress values determined to be the internal stress at the selected area of the sample are averaged to determine the internal stress.

27. The method as recited in claim 25 wherein the calibration curve is generated from at least one bendable test sample, the bendable test sample comprising at least one material and characterized by at least one first stress value.

28. A method for determining internal stress in a sample at high lateral resolution, said sample comprising at least one material and having a planar or smooth surface, said method comprising:

generating a pair of $\Delta(\alpha)$ and $\psi(\alpha)$ calibration curves correlating first ellipsometric $\Delta(\alpha)$ and $\psi(\alpha)$ amplitudes to a set of first stress values, the step further comprising, measuring the set of first stress values in said at least one bendable test sample;

measuring, for each first stress value, a first ellipsometric parameters $\Delta$ and $\psi$ over the range of the rotation angle $\alpha$ by rotating said at least one bendable test sample to generate a set of first ellipsometric parameter $\Delta(\alpha)$ and $\psi(\alpha)$ values;

determining, for each set of the first ellipsometric parameter $\Delta(\alpha)$ and $\psi(\alpha)$ values, the first ellipsometric $\Delta(\alpha)$ and $\psi(\alpha)$ amplitudes representing the difference between a first maximum and a first minimum values defined by the set of first ellipsometric parameter $\Delta(\alpha)$ and $\psi(\alpha)$ values; and correlating the first ellipsometric $\Delta(\alpha)$ and $\psi(\alpha)$ amplitudes to the first stress values to generate the pair of $\Delta(\alpha)$ and $\psi(\alpha)$ calibration curves;

measuring a pair of second ellipsometric parameters $\Delta$ and $\psi$ over a range of rotation angle $\alpha$ at a selected area of the sample by rotating the sample to determine a second ellipsometric $\Delta'(\alpha)$ and $\psi'(\alpha)$ amplitudes, and determining the internal stress at the selected area of the sample from the pair of $\alpha(\alpha)$ and $\psi(\alpha)$ calibration curves by using the second ellipsometric $\Delta'(\alpha)$ and $\psi'(\alpha)$ amplitudes as indices to determine corresponding first stress values from the pair of $\Delta(\alpha)$ and $\psi(\alpha)$ calibration curves.

29. The method as recited in claim 28 wherein a set of second ellipsometric parameter $\Delta'(\alpha)$ and $\psi'(\alpha)$ values is generated from the second ellipsometric parameter $\Delta'(\alpha)$ and $\psi'(\alpha)$ measured over the range of the rotation angle $\alpha$ of the sample.

30. The method as recited in claim 4 wherein the set of second ellipsometric parameter $\Delta'(\alpha)$ and $\psi'(\alpha)$ values defines a second ellipsometric parameter curve, wherein the second ellipsometric $\Delta'(\alpha)$ and $\psi'(\alpha)$ amplitudes are the difference between a second maximum and a second minimum values in the second ellipsometric parameter $\Delta'(\alpha)$ and $\psi'(\alpha)$ curves, respectively.

31. The method as recited in claim 4 wherein the second ellipsometric $\Delta'(\alpha)$ and $\psi'(\alpha)$ amplitude is the difference between a second maximum and a second minimum values defined by the set of second ellipsometric parameter $\Delta'(\alpha)$ and $\psi'(\alpha)$ values, respectively.

32. A method for determining internal film stress on a sample at high lateral resolution, the sample comprising at least one material and having a planar or smooth surface, the sample characterized by a stress optical coefficient tensor c, said method comprising:

measuring ellipsometric parameters $\Delta$ and $\psi$ at a selected area of the sample by rotating the sample as a function of rotation angle $\alpha$ to generate ellipsometric parameter curves $\Delta(\alpha)$ and $\psi(\alpha)$;

determining thickness d of the sample at the selected area of the sample;

determining a dielectric tensor $\tilde{n}$ for the sample from said ellipsometric parameter curves $\Delta(\alpha)$ and $\psi(\alpha)$;

determining the internal film stress at the selected area of the sample in accordance with equation $\tilde{n}=c\,s\,d$, where $\tilde{n}$ is the dielectric tensor $\tilde{n}$, c is the stress optical coefficient tensor, s is the desired stress, and d is the thickness of the sample.

33. The method as recited in claim 32 wherein said ellipsometric parameters $\Delta$ and $\psi$ are measured at a set of polarizer angles.

34. The method as recited in claim 32 wherein said ellipsometric parameters $\Delta$ and $\psi$ are measured for a set of wavelengths.

35. The method as recited in claim 32 wherein the value of said stress optical coefficient tensor c is obtained from a reference table.

36. The method as recited in claim 33 wherein said ellipsometric parameter measuring step comprises:

focusing a linearly polarized incident light onto said selected area of said sample to provide high lateral resolution, said incident light reflecting off of said sample to generate an elliptically polarized light; and measuring said ellipsometric angles $\Delta$ and $\psi$ of said elliptically polarized light.

37. The method as recited in claim 33 wherein said ellipsometric parameters $\Delta$ and $\psi$ are measured at three different polarizer angles.

38. The method as recited in claim 33 wherein said ellipsometric parameters $\Delta$ and $\psi$ are measured at one polarizer angle.

39. The method as recited in claim 32 wherein the thickness d is measured by ellipsometry.

40. The method as recited in claim 32 wherein said internal stress is computed by inversion.

41. The method as recited in claim 32 wherein said internal stress is computed by a fit procedure.

42. The method as recited in claim 32 wherein the sample is a solid sample.

43. The method as recited in claim 32 wherein the sample is not bent.

44. The method as recited in claim 32 wherein the sample is an integrated circuit device.

45. The apparatus as recited in claim 8 wherein the sample is an integrated circuit device.

46. An apparatus for measuring internal film stress on an anisotropic sample at a high lateral resolution, said anisotropic sample comprising at least one layer of a first material disposed on a second material, said apparatus comprising:

an ellipsometer for measuring ellipsometric parameters $\Delta$ and $\psi$ said ellipsometer directing a linearly polarized incident light onto a selected area of said sample to generate an elliptically polarized reflected light, said ellipsometer comparing said linearly polarized incident light and said elliptically polarized reflected light to measure said ellipsometric parameters $\Delta$ and $\psi$, wherein said ellipsometer further comprises:

a light source for generating light;

a polarizer for polarizing said light into said linearly polarized light;

a focusing unit for focusing said linearly polarized light to resolve high lateral resolution;

an x-y-z stage for changing the position of said sample in x, y, and z directions, said sample being disposed over said x, y, and z stage wherein said linearly polarized light reflects off of said sample to generate said elliptically polarized reflected light;

a microscope aligned to said center of rotation of said rotation stage for selecting an area of said sample to determine internal film stress thereon;

a rotating analyzer for comparing said first polarization state to said second polarization state to generate said ellipsometric parameters $\Delta$ and $\psi$ in terms of the polarization state, said rotating analyzer for transforming said delta and phi angles into a light intensity;

a detector for detecting said light intensity to generate ellipsometric parameters Δ and ψ; and a control unit coupled to said detector, said rotating analyzer, said z-y-z stage, and said rotating stage for measuring and correlating the ellipsometric parameters Δ and ψ from said detector to the angle of rotation, α, to determine stress at said selected area of said sample and a rotating stage rotatably disposed below said ellipsometer for rotating said sample so as to vary an angle of rotation α about a center of rotation axis, said center of rotation axis being aligned with said ellipsometer wherein said ellipsometer correlates said ellipsometric parameters Δ and ψ to said angle of rotation α to determine the internal film stress at said selected area of said sample at a high lateral resolution.

47. The apparatus as recited in claim 46 wherein said light source is a laser beam.

48. The apparatus as recited in claim 46 wherein said light source is a polychromatic light source.

49. The apparatus as recited in claim 47 wherein said light source further includes a monochromator.

50. The apparatus as recited in claim 47 wherein said light source further includes a diode-detector array.

51. The apparatus as recited in claim 46 wherein said focusing unit is a lens.

52. The apparatus as recited in claim 46 wherein said focusing unit is a lens system.

53. The apparatus as recited in claim 46 wherein said focusing unit is a microscope objective.

54. The apparatus as recited in claim 8 wherein the sample is a solid sample.

55. The apparatus as recited in claim 8 wherein the sample is not bent.

* * * * *